United States Patent
Vaidyanathan et al.

(10) Patent No.: US 7,133,784 B2
(45) Date of Patent: Nov. 7, 2006

(54) PROCESS AND METHOD FOR CHEMICAL MANUFACTURING USING TRANSFORMATION OF ON-LINE INSTRUMENTATION DATA

(75) Inventors: Ramaswamy Vaidyanathan, Aurora, IL (US); William D. Stephens, Batavia, IL (US); David R. Van Hare, Parkville, MO (US)

(73) Assignee: BP Corporation North America, Inc., Warrenville, IL (US)

( * ) Notice: Subject to any disclaimer, the term of this patent is extended or adjusted under 35 U.S.C. 154(b) by 0 days.

(21) Appl. No.: 10/695,319

(22) Filed: Oct. 28, 2003

(65) Prior Publication Data

US 2004/0133363 A1    Jul. 8, 2004

Related U.S. Application Data

(60) Provisional application No. 60/421,648, filed on Oct. 28, 2002.

(51) Int. Cl.
    *G01N 31/00*    (2006.01)
(52) U.S. Cl. .............................. 702/30; 702/32; 700/266
(58) Field of Classification Search ............ 702/22–32, 702/179, 181, 182; 700/42, 50, 51, 266; 436/37; 706/904, 906; 526/59, 60
See application file for complete search history.

(56) References Cited

U.S. PATENT DOCUMENTS

| | | | |
|---|---|---|---|
| 3,356,667 A | 12/1967 | Smith et al. ................... 526/60 |
| 3,506,640 A | 4/1970 | Reid et al. ..................... 526/60 |
| 3,759,820 A | 9/1973 | Boyd ........................... 208/64 |
| 3,891,836 A | 6/1975 | Lee ............................... 700/3 |
| 3,976,981 A * | 8/1976 | Bowden ..................... 700/10 |
| 4,349,869 A | 9/1982 | Prett et al. .................... 700/39 |
| 4,448,736 A | 5/1984 | Emery ........................ 264/40.1 |
| 4,469,853 A | 9/1984 | Mori ............................ 526/59 |
| 4,616,308 A | 10/1986 | Morshedi et al. ............. 700/39 |
| 4,888,704 A | 12/1989 | Topliss et al. ............... 700/269 |
| 5,155,184 A | 10/1992 | Laurent et al. ............... 526/59 |
| 5,324,755 A * | 6/1994 | Kilius et al. ................. 523/214 |
| 5,387,659 A | 2/1995 | Hottovy et al. .............. 526/59 |
| 5,408,181 A * | 4/1995 | Dechene et al. ............. 324/307 |
| 5,504,166 A | 4/1996 | Buchelli et al. ............. 526/60 |
| 5,644,007 A | 7/1997 | Davidson et al. ............ 526/64 |
| 5,650,722 A | 7/1997 | Smith et al. |
| 5,675,253 A | 10/1997 | Smith et al. |
| 5,684,580 A | 11/1997 | Cooper et al. ............. 356/301 |
| 5,830,954 A | 11/1998 | Hayashi et al. ............. 526/60 |

(Continued)

FOREIGN PATENT DOCUMENTS

EP     0398706 A2    11/1990

(Continued)

OTHER PUBLICATIONS

"Nonlinear Material Balance Technique to Control Reactor Gas Composition," IBM Technical Disclosure Bulletin, IBM Corp. New York, US, vol. 40, No. 8, Aug. 1, 1997, p. 13; XP000735561; ISSN: 0018-8689.

*Primary Examiner*—Marc S. Hoff
*Assistant Examiner*—Manuel L. Barbee
(74) *Attorney, Agent, or Firm*—James R. Henes

(57) ABSTRACT

A method for providing improved estimates of properties of a chemical manufacturing process is disclosed. The method regesses process variables with scores or other gains obtained from the mathematical transformation of data obtained from an on-line analyzer. Chemical manufacturing processes using the method also are disclosed.

27 Claims, 4 Drawing Sheets

U.S. PATENT DOCUMENTS

| | | | |
|---|---|---|---|
| 5,877,954 A | 3/1999 | Klimasauskas et al. | 700/29 |
| 5,933,345 A | 8/1999 | Martin et al. | 700/44 |
| 6,072,576 A * | 6/2000 | McDonald et al. | 356/300 |
| 6,122,555 A | 9/2000 | Lu | 700/9 |
| 6,144,897 A | 11/2000 | Selliers | 700/269 |
| 6,204,664 B1 | 3/2001 | Sardashti et al. | |
| 6,479,597 B1 * | 11/2002 | Long et al. | 526/59 |
| 6,590,131 B1 * | 7/2003 | McGinn et al. | 585/501 |
| 6,654,649 B1 | 11/2003 | Treiber et al. | |
| 2002/0156205 A1 | 10/2002 | Long et al. | 526/60 |
| 2003/0073787 A1 * | 4/2003 | Stephens et al. | 526/65 |
| 2004/0233425 A1 * | 11/2004 | Long et al. | 356/301 |

FOREIGN PATENT DOCUMENTS

| | | |
|---|---|---|
| EP | 0486262 A1 | 5/1992 |
| WO | 9324533 | 12/1993 |
| WO | 9526990 A1 | 10/1995 |
| WO | 9641822 A1 | 12/1996 |
| WO | 0149751 A1 | 7/2001 |
| WO | 0151589 A1 | 7/2001 |
| WO | 0182008 A1 | 11/2001 |
| WO | 0216932 A1 | 2/2002 |
| WO | 3026791 A1 | 4/2003 |

* cited by examiner

TO PURGE COLUMN

PROCESS AND METHOD FOR CHEMICAL MANUFACTURING USING TRANSFORMATION OF ON-LINE INSTRUMENTATION DATA

This application claims the benefit of Provisional Application No. 60/421,648, filed Oct. 28, 2002.

FIELD OF THE INVENTION

The invention relates to chemical manufacturing process control. More specifically, the invention relates to the use of information obtained by mathematical manipulation of on-line analyzer data. This information describes sources of variability in manufactured materials, which can be used to improve the performance of controllers or models used in a chemical manufacturing process.

BACKGROUND OF THE INVENTION

Chemical manufacturing processes typically operate in the liquid or gas phase within a set of operating conditions such as temperature, pressure, and catalyst concentration to produce a material having a desired set of physical and chemical properties.

For example, one or more olefins can be reacted in a liquid or gas phase reactor in the presence of a catalyst to produce a polyolefin or other polymer. A variety of polymers having different properties can be manufactured in the same reactor by altering the operating conditions, types and ratios of reactor feedstock, catalyst and additives. Such parameters are referred to herein as reactor process variables. One polymer property often of great interest is polymer melt flow rate.

Modern chemical reactors typically employ computer-based control of some type to maintain product quality and to transition operation from the manufacture of one product to another. Where the reactor is used to manufacture polypropylene, the melt flow rate can be altered if the control program alters, for example, the hydrogen to propylene ratio present in the reactor.

The types of control used in modern reactors can range from one or more control loops using relatively simple proportional integral derivative (PID) or fuzzy logic controllers to sophisticated state of the art predictive control programs. In some cases, the use of linear regression of process variables in combination with information obtained from on-line analyzers provides a useful method for process control.

A goal of most any polymer control system or model will be to produce a material having a specified set of properties, including polymer melt flow rate. Because loop control and models both tend to represent imperfect descriptions of behavior, the properties of materials produced using control based on these principles tend to differ somewhat from the desired values of the actual properties as measured in the lab.

Where techniques such as the regression of process variables with product characteristics are used, the time required to identify the difference between predicted and measured polymer properties has led to various efforts to develop on-line instrumentation capable of measuring directly or inferring a product quality during polymer production. For example, it is known to use various on-line viscometers to directly measure rheometric properties of polymers. Alternatively, on-line instruments such as Fourier transform infrared spectrometers ("FTIRs"), near infrared spectrometers ("NIRs"), ultraviolet-visible ("UV-VIS") spectrometers, Raman spectrometers and nuclear magnetic resonance spectrometers ("NMRs" or "IMRs") have been used with varying degrees of success to infer material properties, such as melt flow rates, from the types of data that can be generated by these instruments and their associated data analysis software. Inferences of a property such as melt flow rate from spectrometric data typically is accomplished using advanced mathematical techniques such as multivariate curve fitting, neural networks, Principal Component Regression (PCR), or Partial Least Squares Regression Analysis (PLS), to transform the raw spectrometric data into an estimate of the desired physical property. Additional background information concerning PCR and PLS can be found in "Partial Least Squares Regression: A Tutorial", Analytica Chimica Acta 185 (1986) 1–17, by P. Geladi and B. R. Kowalski.

In PCR and PLS, the spectrometric data are decomposed into two matrices, a "scores" matrix and a "loadings" matrix. The loadings matrix is a vector matrix containing the minimum number of vectors that adequately describe the variability in the spectral data while providing the desired level of predictive ability in the resulting model. The scores matrix is a scalar matrix that contains the contribution of each of the loadings vectors to each sample spectrum.

Thus, each sample spectrum in the calibration set can be reconstructed from a linear combination of the products of scores and loadings. For example, a four factor PCR or PLS model will have four loadings vectors and each sample can be described by four scalar values (the scores). A subset of one or more of these scores typically describes most of the variability attributable to a property such as melt flow rate. Additional information concerning the development and use of these techniques can be found in "Chemometrics: Its Role in Chemistry and Measurement Sciences", *Chemometrics and Intelligent Laboratory Systems*, 3 (1988) 17–29, Elsevier Science Publishers B.V., and "Examining Large Databases: A Chemometric Approach Using Principal Component Analysis", *Journal of Chemometrics*, Vol. 5, 79 (1991), John Wiley and Sons, both authored by Robert R. Meglen, the disclosure of each being incorporated by reference in its entirety.

In some cases, process control engineers have attempted to enhance spectral analyzer results by performing regression analysis of local process variables measured in-situ or in the immediate vicinity of the analyzer with scores resulting from the estimation of a property, such as Mooney viscosity, by on-line instrumentation. One such approach is described in U.S. Pat. No. 6,072,576 to McDonald, et al, the disclosure of which is hereby incorporated by reference. While this method may lead to improved process control in some cases, the industry desires new, more powerful approaches to integrating on-line instrumentation and process control. Such improved techniques would be useful, for example, to minimize variability in manufactured materials, or to minimize transition times when switching from the manufacture of one material to another.

SUMMARY OF THE INVENTION

We have found that improvement in process control may be provided in estimating product properties or process conditions of state by regressing certain "scores" resulting from a mathematical technique used to derive distinct sources of variability in on-line sample data with at least one, and preferably several chemical process variables measured upstream or downstream of the analyzer to yield an enhanced estimate of a process property such as melt flow rate.

This enhanced estimate then can be used directly for process control, such as being used as an input to a PID or fuzzy logic control loop, or in connection with other models used in the control of the chemical process.

It should be noted that the use of one or more physical measurements obtained at or near an on-line analyzer for the purpose of improving the property measurement ability of the analyzer, whether or not such data is mathematically transformed by linear regression or other method, is not considered to be regression of process variables with mathematically transformed process data as contemplated by our invention.

In one embodiment of our invention, we obtain an improved estimate of a product property, or process condition or state (hereafter generically a "property"), useful in a chemical manufacturing process. The improved estimate is obtained by regressing one or more process variables, and preferably a reactor process variable, with one or more scores correlative to the property. The scores are obtained by mathematically transforming data obtained from an on-line analyzer. The improved estimate of the property may then be used by a controller to provide for improved plant performance.

As used in this application, a "controller" can be any device, including, but not limited to, hardware or software, capable of accepting an estimate of a desired property and using that estimate to alter its control output. For example, a controller can be a simple loop controller based on PID or fuzzy logic, or a multivariate predictive optimizer controller, as discussed in more detail below.

"Chemical reactor" means any vessel in which a chemical feedstock is converted into a different chemical effluent, whether or not in the presence of a catalyst or other materials, and without regard for whether the reaction occurs in a liquid, solid or gaseous phase, or as a supercritical fluid, or combinations thereof.

When scores or other "gains" as described below are regressed with process variables, it means that the scores or gains can be regressed by any of the linear or non-linear regression techniques known to those skilled in the modeling art.

"Mathematical transformation" means mathematical manipulation of sample data from an on-line instrument by any method that yields a matrix of scores representative of a set of vectors (the loadings vectors), each vector capturing a distinct source of variability in the measured samples. In other words, a mathematical transformation operates on a set of data (such as a set of free induction decay curves from a nuclear magnetic resonance analyzer) to reduce the data to scores and loadings matrices that represent a simplified data set that when taken together can be used to reproduce the raw data to a high degree of certainty, but which reduce the number of dimensions required to describe the data set to a lower number of dimensions better suited for use in control or prediction applications.

"On-line analyzer" refers to any instrument capable of producing data that can be transformed into scores that can be correlated to a property in real time, or in sufficiently near real time so as to be useful for process control purposes. An on-line analyzer useful for this purpose typically will be any analyzer that can provide an estimate of a property to the control system faster, more frequently or more conveniently than the system can be provided the measured value of that property from samples drawn and analyzed in the laboratory.

Typically, such on-line analyzers are spectral analyzers such as NMR, IR, NIR, UV-VIS or Raman spectrometers, as the spectra generated by these devices lend themselves well to the application of the mathematical techniques described above, but the term "on-line analyzer", as used in this invention, includes any analyzer capable of generating a data set that can be subjected to the mathematical transformation processes mentioned above.

In some embodiments of this invention, the free induction decay curves ("FIDs") obtained from on-line nuclear magnetic resonance measurements of a chemical product, such as a propylene-containing polymer, are mathematically transformed by Partial Least Squares analysis to obtain scores which are regressed with process variables to determine melt flow rate.

In yet another embodiment of our invention, a chemical manufacturing process uses an on-line analyzer to collect data for a chemical material at a point within the manufacturing process; mathematically transforms the data to produce scores related to the chemical material; regresses the scores with one or more process variables to produce an estimate of a property of interest for the chemical material; and inputs the estimated property into a controller used in the chemical manufacturing process. The controller output can then be varied in response to the estimated property to cause the property of interest to move toward a desired value.

As used in this application, "process model" means any process model that generates predicted values of one or more process variables at the then current time to determine whether control actions should be taken by one or more controllers at about the same point in time. Such controllers may be linear or nonlinear. The term "non-linear", when used in describing a controller, means a controller that is capable of optimizing non-linear relationships, either directly, but more typically indirectly, such as by approximating solutions to non-linear relationships, using multiple equations to model a non-linear relationship over discrete ranges of variable values.

In preferred embodiments, a predictive process model is used in association with one or more multivariate predictive optimizer controllers.

As used in this application, "predictive process model" means any forward-looking process model that generates predicted values of one or more process variables at a future point in time to determine whether control actions should be taken by one or more controllers at a present or a future point in time. As with process models generally, such controllers may be linear or nonlinear. In some preferred embodiments of the invention, a predictive process model is associated with one or more multivariate predictive optimizer controllers.

A "multivariate predictive optimizer controller" is a controller that is based on multi-variable dynamic (i.e., time-variant) expressions, which is the compiling or calculation of a matrix of values or functions which relate a plurality of manipulated and, optionally, disturbance variables, to a plurality of control variables, and optionally, to constraint variables, in such a manner as to facilitate prediction of state variables at future points in time and to enable control of a system based in whole or in part on such predictions.

In some preferred embodiments of these inventions, the chemical reactor is a polyolefin reactor. As used herein, a "polyolefin reactor" is a chemical reactor in which at least fifty weight percent of the reactor feedstock is propylene and/or ethylene, which is reacted in the presence of a catalyst to produce a polyolefin comprising polypropylene, polyethylene or co-polymers thereof. Reactor types typically used for the production of polyolefins include gas phase fluidized bed reactors, gas phase subfluidized bed reactors, stirred tank reactors, liquid pool reactors, gas loop reactors having one or more fluidization domains, such as multi-zone circulating reactors having a fluidization zone and a packed bed zone where polymer powder flows by the force of gravity, and supercritical loop reactors.

Preferably, polyolefin reactors use catalysts selected from the group consisting of Ziegler-Natta, late transition metal, and metallocene catalysts, and more preferably, the manufacturing process occurs at least partially in the gas phase. This embodiment is particularly useful for the manufacture of polyolefins and olefin copolymers, and in particular, ethylene and propylene-containing polymers or copolymers. The invention particularly can be used effectively in connection with one or more horizontally agitated, sub-fluidized bed gas phase reactors.

DETAILED DESCRIPTION OF THE INVENTION

Applicants' invention is described below in detail in connection with the manufacture of polypropylene. Applicants' invention is useful in many chemical manufacturing environment, and can be adapted to other processes by those skilled in the art using the teachings contained in this application.

Figure 1:
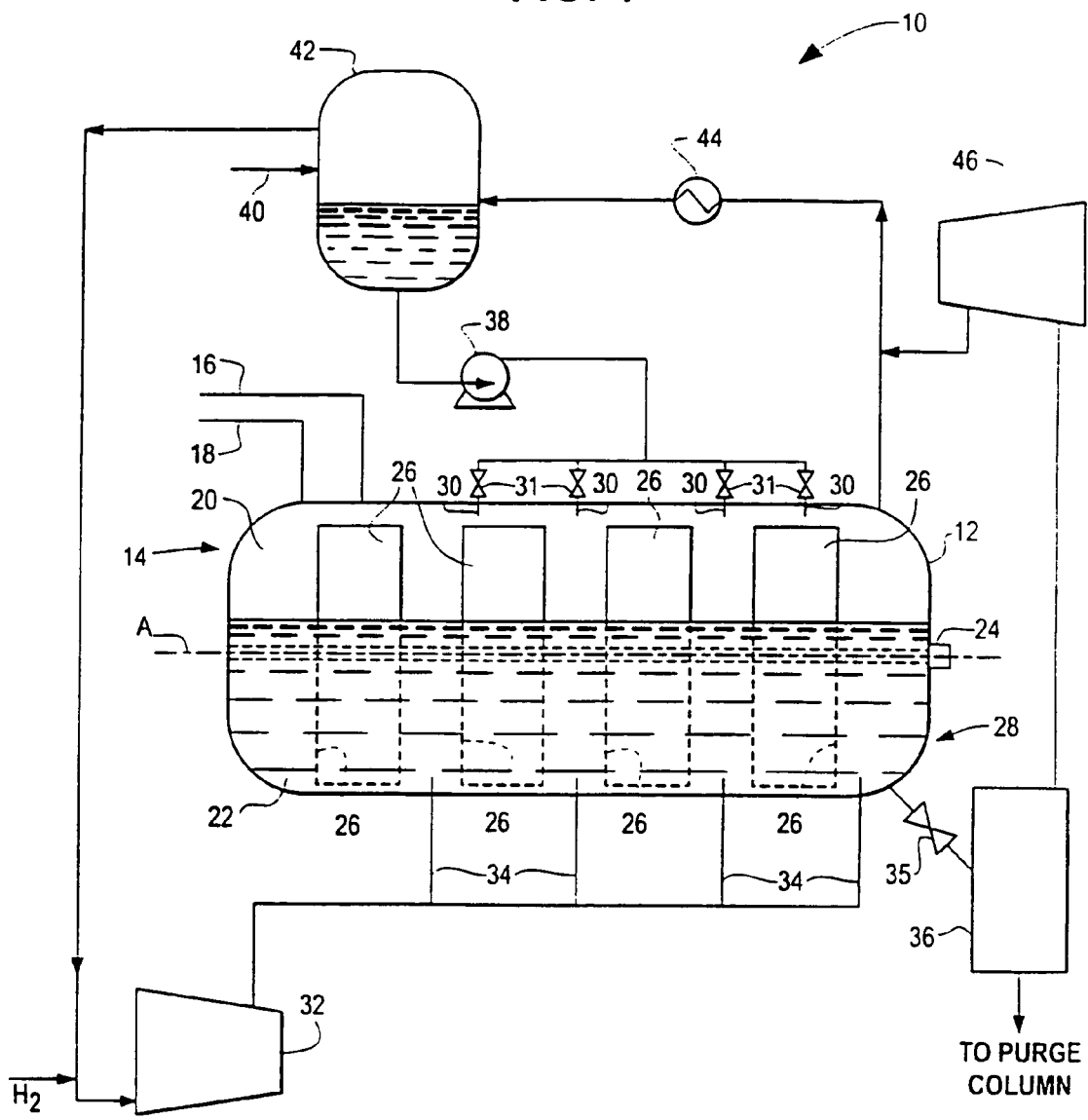
FIG. 1 is a diagram showing a horizontally agitated subfluidized bed reactor and associated equipment for the manufacture of polypropylene.

FIG. 1 illustrates a horizontal, mechanically agitated, sub-fluidized bed reactor system 10 including certain key associated equipment used for the manufacture of polypropylene.

Polymerization of monomer feedstock occurs in a horizontal, cylindrical reactor vessel 12. Catalyst, co-catalyst and modifiers can be fed at a continuously variable rate separately into an inlet end 14 of vessel 12 through feedlines 16 and 18.

During steady state operation, polymerization begins in a vapor space 20 located in the upper portion of vessel 12, and, as particle size increases and particles settle, continues in a particulate bed 22 occupying the lower portion of vessel 12. An agitator 24 is located along the longitudinal axis A of vessel 12. Paddles 26 of agitator 24 stir particulate bed 22 as agitator 24 is turned, thereby promoting mixing and a plug flow movement of material in particulate bed 22 towards a discharge end 28 of vessel 12.

Monomer and condensed liquid from vapor/liquid separator 42 (collectively referred to as "quench liquid") are added into vapor space 20 of vessel 12 through quench nozzles 30 longitudinally located in vapor space 20 near the top of vessel 12. The liquid added through nozzles 30 cools hot particles located on the upper surface of particulate bed 22, and paddles 26 subsequently drive these cooled particles, and any remaining liquid monomer, into particulate bed 22 to continue the exothermic polymerization reaction and to further cool bed 22. The flow of liquid into vessel 12 can be controlled regionally within vessel 12 by quench control valves 31.

Recycled reactor vapor can be introduced through compressor 32 into a lower portion of bed 22 through gas inlets 34. Hydrogen also can be introduced into the lower portion of bed 22 through gas inlets 34 by adding hydrogen at or near the inlet or outlet of compressor 32.

Polymer product is removed from discharge end 28 of vessel 12 through one or more discharge valve(s) 35. The discharged product passes through a solid/gas separator 36 (also referred to as the "baghouse"), after which the discharged solid product is transferred to a purge column (see FIG. 2), while the separated gas is routed to offgas compressor 46 to be compressed prior to condensation for make-up to vessel 12.

Reactor offgas cooler condenser 44 condenses vapor drawn directly from reactor vapor space 20, as well as condensed offgas removed from solid/gas separator 36, which was compressed by offgas compressor 46. Vapor and liquid feed to vessel 12 is accomplished using liquid/vapor separator 42. Liquid for feed to vessel 12 through pump 38 is a combination of condensate and fresh monomer make-up through monomer make-up line 40.

Under nominal operating conditions, the reactor system described above operates at pressures of from about 1400 to 2800 kPa (200 to 400 psig) and at temperatures of from about 50 to 90 degrees Centigrade (122 to 194 degrees Fahrenheit). The volume of the particulate polymer bed typically occupies between about 40 to 80 percent of the volume of vessel 12.

Reactor system 10 typically can be used to produce homopolypropylene or random copolymers of propylene and other olefins, such as ethylene. Control of such a reactor system typically involves the use of an empirical, semi-empirical or first principles reactor process model, as discussed in greater detail below. The process model advantageously employs an estimate of polymer melt flow rate obtained in part from scores resulting from the mathematical transformation of FID curve data obtained from an on-line NMR analyzer located as shown in FIG. 2.

Control of a reactor system 10 typically requires manipulation of reactor process variables such as:

a) catalyst flow to control production rate;
b) hydrogen concentration to control molecular weight or melt flow rate;
c) comonomer feed and concentration (when making random copolymers) to control product properties;
d) cocatalyst to catalyst ratio;
e) cocatalyst to electron donor ratio when using catalyst systems having co-catalysts such as tri-alkyl aluminum and external electron donors; and
f) various gas concentrations and ratios in the recycle loops to determine the proper make-up of raw and recycled materials to maintain the desired in-reactor concentrations.

Figure 2:
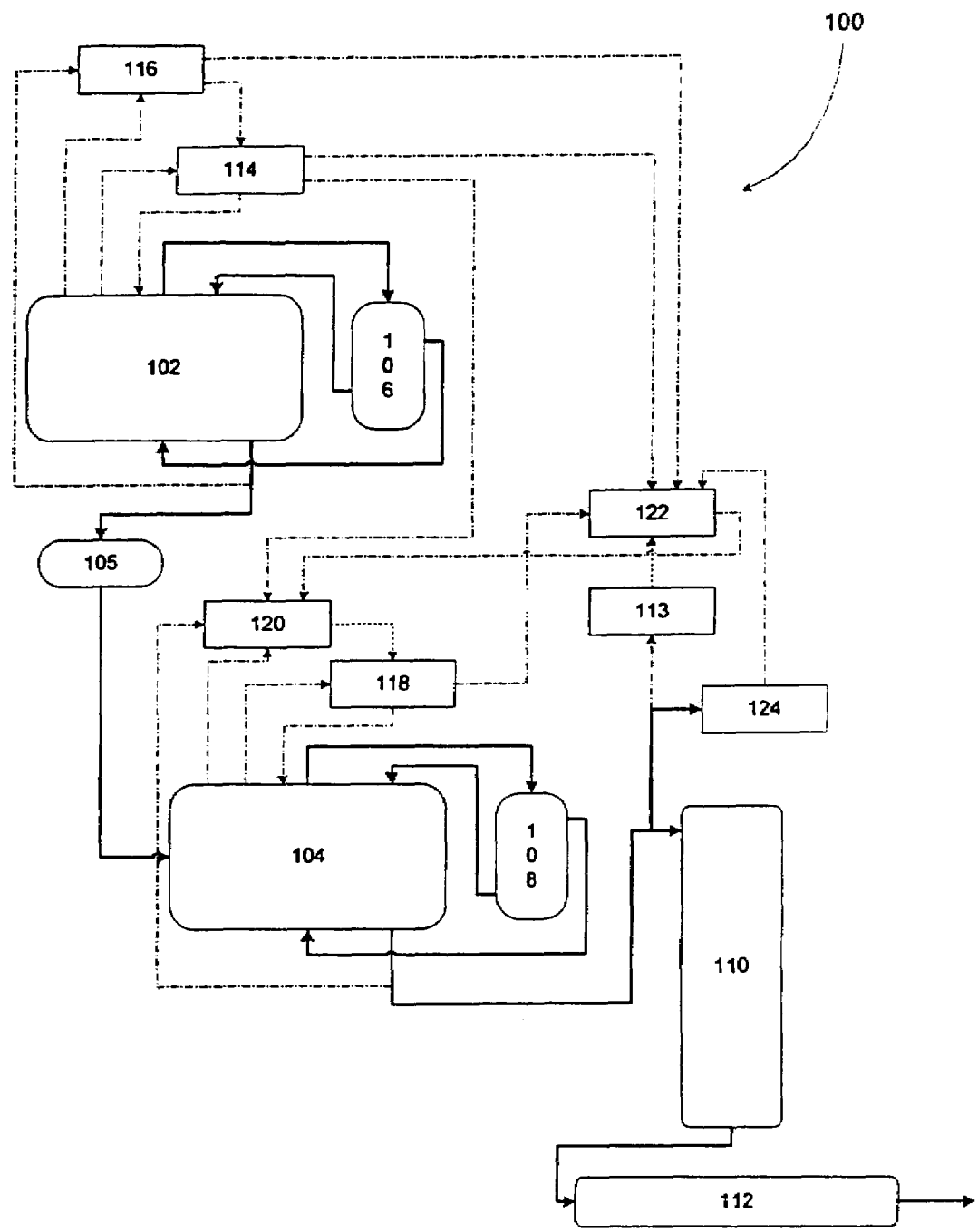
FIG. 2 is a schematic diagram of a system for making polypropylene. The system uses two reactors of the type described in connection with FIG. 1. The system employs an on-line analyzer capable of providing sample data, which can be mathematically transformed to yield scores that can be regressed with process variables to estimate melt flow rate.

FIG. 2 is a simplified schematic diagram of a chemical manufacturing process 100 capable of making homopolymers, random copolymers and impact copolymers of polypropylene. In FIG. 2, the solid lines indicate the flow of materials, while the dashed lines indicate the flow of information. As will be recognized by those skilled in the art, random copolymers typically are those materials formed by the introduction of two or more polyolefins in a single reactor, and impact copolymers typically are those materials formed by first producing a polymer such as a polypropylene material in a first reactor or reaction zone, which is transferred into a second reactor or reaction zone to incorporate an impact-modifying material formed in the second reaction zone, such as an ethylene-propylene ("EPR") rubber. System 100 physical plant equipment includes a first reactor 102, a second reactor 104, a first reactor liquid gas separator 106, a second reactor liquid gas separator 108, a purge column 110 for degassing residual hydrocarbons from the impact copolymer powder produced in reactor 104, an extruder 112 for converting the degassed powder into pellets, as are typically used by the conversion industry, and an on-line NMR melt flow analyzer 113 located between the baghouse (see element 36 of FIG. 1) and purge column 110 as well as a laboratory 124 which performs product analysis of samples collected at the point of the NMR analyzer 113. System 100 can also include non-linear multivariable predictive optimizer controllers, in this case the four optimizers 114, 116, 118 and 120, as well as a computer 122 capable of performing process control, but are not necessarily part of system 100. Reactors 102 and 104 typically operate in the manner described in detail in connection with the description of system 10 of FIG. 1 and with auxiliary equipment of the type described in connection with FIG. 1. The operation of horizontal gas phase reactors of this type is well known to those skilled in the art, and is described in our U.S. Pat. Nos. 4,888,704 and 5,504,166, the disclosure of each being hereby incorporated by reference.

Reactors 102 and 104 operate using a process control program that requires an estimate of product melt flow rate as measured between baghouse 36 (see FIG. 1) and purge column 110 (see FIG. 2).

Use of our invention to obtain good estimates of the melt flow rate is demonstrated by Example 1, below.

EXAMPLE 1

A variety of impact copolymers of polypropylene were manufactured over a three month period using a two reactor system such as the one described in FIGS. 1 and 2 above.

In Example 1, a calibration data set was collected during the three month period. There were 425 data points in the calibration set. All calibration data have been adjusted by a time lag approximately equal to the time required for material produced in the reactor to pass through system 100 to the point where the on-line analyzer is located so that on-line data will be representative of material produced in the reactors at an earlier point in time. Additionally, process data has been averaged over about a one half to one hour period around the time selected as representative of the manufactured material. Similar time lags and time averaged measurement of process conditions preferably would be used when implementing the embodiment of the invention described in Example 1, and preferably are employed wherever on-line instrument data is acquired at a point located substantially downstream (with respect to time) from the point where process conditions are measured.

For the validation set, data were collected for a one-year period. Validation data have been filtered against the following criteria to ensure stable process conditions. All process and scores data are based on 8-hour averages. For process data, each 8-hour interval was broken up into eight 1-hour sub-intervals. The average values of the 1-hour sub-intervals could not deviate by more than a specified percentage from the average for the full 8-hour interval otherwise, the data were excluded. For the scores data, outliers were eliminated using the Mahalanobis distance as a criterion. Additional information concerning the use of the Mahalanobis distance can be found in "Multivariate Data Analysis, $5^{th}$ Edition" by J. F. Hair, Jr., R. E. Anderson, R. L. Tatham, and W. C. Black; Prentice Hall (pub), 1998, pp. 66, 219, 224. After outlier removal, there were 569 data points in the validation set.

The reactor system was fitted with an on-line nuclear magnetic resonance measurement system available from Oxford Instruments of North Andover, Massachusetts as the Oxford Instruments MagneFlow Rack Mount analyzer. This system was used to provide direct estimates of melt flow rate by performing a PLS regression of free induction decay curves generated by the analyzer.

NMR measurements were performed every six to eight minutes on a fresh polymer sample extracted from the process and subsequently handled as described below.

A 300 ml powder sample was extracted from the process and educted to the on-line NMR system where the powder was separated from the motive gas by a cyclone separator. The powder dropped by gravity into a pre-heater chamber where it was fluidized with hot nitrogen until it reached a designated temperature of 71 degrees Centigrade. A valve in the bottom of the preheater then opened and dropped the sample into the NMR probe located between the pole faces of a permanent magnet.

The sample was checked for adequate size and, if adequate, the measurement sequence was started. During the measurement sequence, the sample was subjected to a series of 90-degree radio frequency (RF) pulses and the free induction decay (FID) data were collected after each pulse. The FID signals for each sample were averaged and then sent to the NMR control computer for score generation and prediction of properties. The sample was then educted from the NMR probe and returned to the process stream.

More specifically, partial least squares analysis was used to obtain scores from the NMR data. The scores were then combined with process model data and the combined process model data and scores non-linearly regressed to determine statistically significant terms. While non-linear regression of NMR data is used in this Example, it should be noted that linear regression can be used instead of non-linear regression where appropriate. When a statistically insignificant term was identified, that term was dropped from the combined score and process model, and the regression run again. This process was repeated until only statistically significant terms remained in the combined equation.

Scores from the mathematical transformation of on-line NMR process data were selected by empirical evaluation of the partial least squares analysis of the data in a manner known to those skilled in the art. Typically, the results of the data analysis package will yield a number of scores, each of which correlates to a distinct (i.e. substantially independent) source of variability (represented by factors or loadings from PLS regression) in the analysis of the on-line NMR sample. The control engineer will take the scores and check to see which terms are most highly correlated to variability in melt flow rate (or other property of interest) and select those scores that represent statistically meaningful correlations to melt flow for use in the combined model.

It is important to note that the scores selected are not necessarily those from the instrument data that describe the highest variability of the sample data, but those that when combined with process data show the highest correlation to observed melt flows. Thus, scores were selected because they were the only statistically significant results showing a high degree of correlation between observed and predicted process model melt flow rate when combined with the process data.

The scores were linearly regressed with several process variables used in connection with the foregoing process models. The variables combined with the scores for regression included Al/Mg ratio, first reactor catalyst yield, second reactor incremental catalyst yield, first reactor offgas temperature, hydrogen to propylene ratio for the first reactor, hydrogen to propylene ratio for the second reactor, ethylene to propylene ratio for the second reactor, and percent rubber in the final impact copolymer product. As used in this application, each of these variables relates to operation of one or both of the reactors, and as such is a reactor process variable.

Of these variables, Al/Mg ratio, first reactor offgas temperature, and second reactor incremental catalyst yield were statistically insignificant when linearly regressed with the NMR scores and used to predict melt flow rate. All four scores obtained from analysis of the NMR data proved to be statistically significant.

Figure 3:
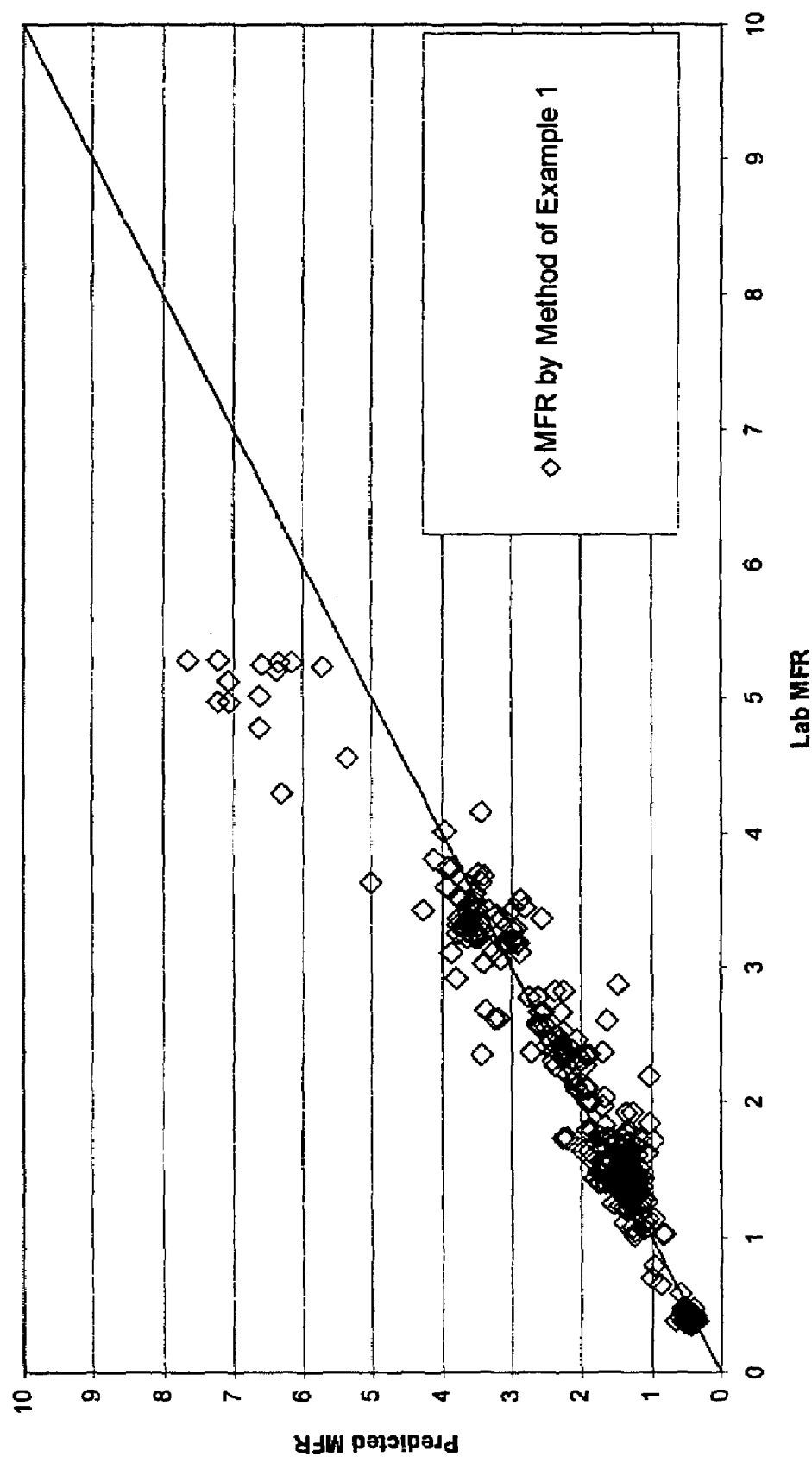
FIG. 3 is a plot of melt flow rates of Example 1.

FIG. 3 is a plot of predicted melt flow rate vs. melt flow rate as measured in the lab for the calibration set of 425 data points. The data points represent predicted melt flow rate by a model developed using the linear regression approach described above that regresses scores with process data (plotted as diamonds on FIGS. 3 and 4).

Figure 4:
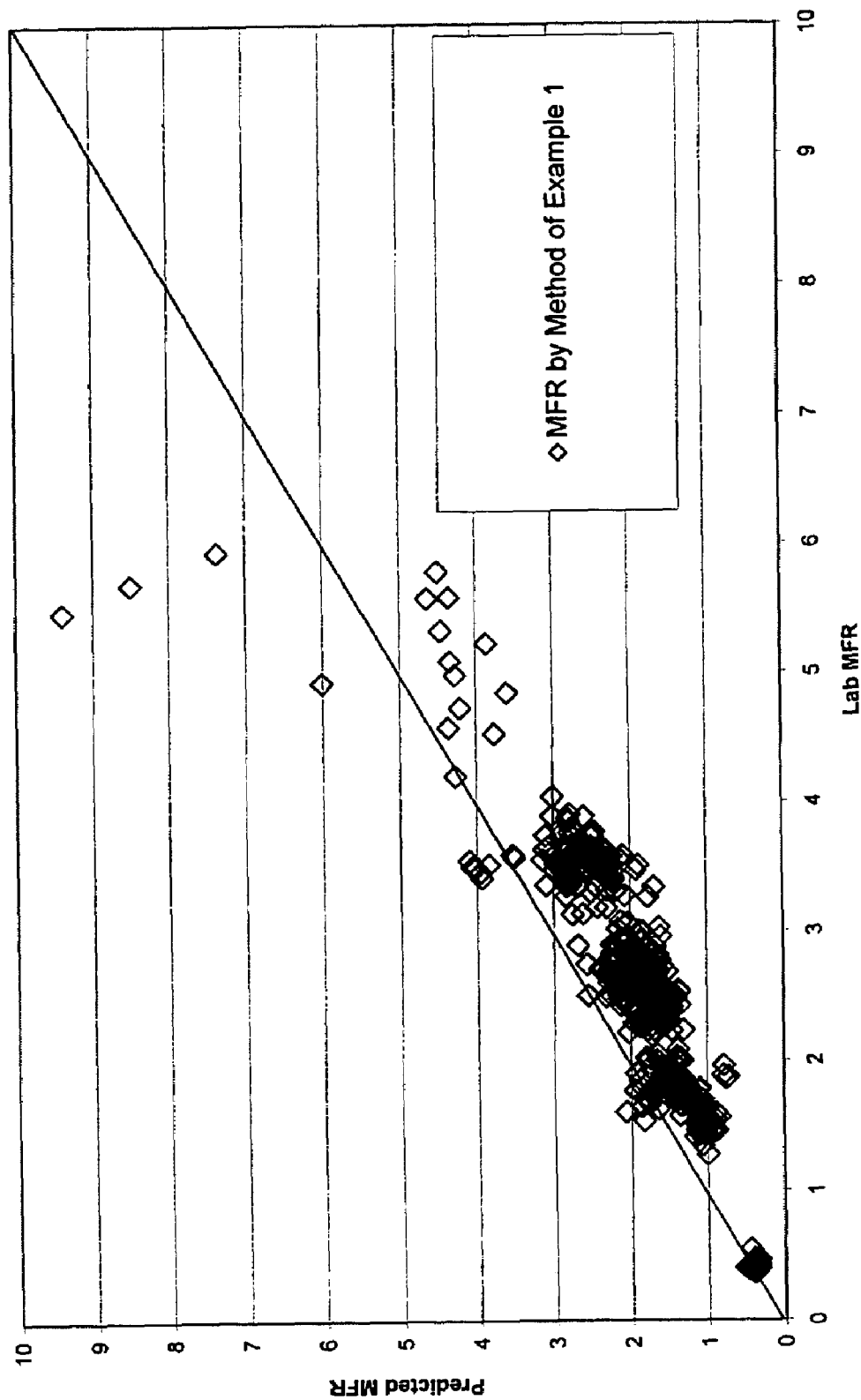
FIG. 4 is a plot of predicted melt flow rates using the model created in connection with Example 1.

As can be seen by comparing the data points on FIG. 3, the model developed by regressing scores and process data yielded 340 data points out of a total of 425 data points that were within ±20 percent of the laboratory value. FIG. 4 is a plot of laboratory melt flow rate and validation data for predicted melt flow rates using the models created in connection with FIG. 4. The validation was done with 569 data points obtained during a twelve-month period of time after collection of the data used in model building. As can be seen from FIG. 4, predictions of melt flow rate using model validation data yielded 199 data points out of 569 data points that were within ±20 percent of the laboratory value.

Quantitatively, the root mean square error of prediction for the NMR data, and for the approach in accordance with Example 1, are, respectively, 147.6% and 27.1%. While more sophisticated modeling and control methods may yield improved performance, we believe the simple method of Example 1 can be advantageously applied in many circumstances.

While the foregoing Example of the invention illustrates the use of the invention to produce improved estimates of melt flow rate of impact copolymers of polypropylene, the invention may be used in a wide variety of chemical manufacturing applications, such as in the manufacture of a wide variety of chemicals including terephthalic acid, polystyrene, polymers of propylene, or ethylene, or alpha-olefin monomers containing from 4 to 20 carbon atoms, including combinations of two or more of the foregoing olefins or alpha olefins, polyvinyl chloride and polyethylene terephthalate, or combinations of any of the foregoing. Examples of olefinic polymers include polymers containing at least fifty weight percent of material originating as propylene monomer units and less than fifty weight percent (for example one, two, five or more weight percent) of material originating as monomers of a second olefin such ethylene, or polymers containing at least fifty weight percent of material originating as ethylene monomer units and less than fifty weight percent (for example one, two, five or more weight percent) of material originating as C4, C6 or C8 alpha-olefins.

It should be noted that combinations and/or transforms of scores (for example, cross products, reciprocals, squares, and other mathematical transforms of the scores, collectively referred to hereafter as transformed scores) may be used as the scores in the invention as described above if the use of the transformed scores yield improved predictive ability of the regressed scores and process variables in accordance with the invention.

As mentioned earlier, "coefficients" from multivariate curve fits and "weights" or "hidden node outputs" from neural network analysis are analogous to scores in the Example discussed above. Thus, like scores, they can be used to mathematically transform and/or reduce the dimensionality of process analyzer data. When using coefficients or weights or hidden node outputs in the invention, they are used in the same manner as scores or their transforms or combinations are used in the Examples above. As used in this application and elsewhere in the art, scores, coefficients, neural network weights and hidden node outputs are referred to generically as "gains".

Other specific examples where our invention can be employed include estimation of melt index or density for polyethylene, and estimates of the amount of alpha olefin comonomers incorporated into a copolymer material, such as C4, C6 and/or C8 content in high density polyethylene, medium density polyethylene, and/or linear low density polyethylene, where the manufactured material typically contains at least fifty weight percent of material originating as ethylene monomer units.

Other applications for our invention will be apparent to those skilled in the art upon their reading of the descriptions contained herein. Our invention, therefore, is not limited to any particular manufacturing process, process variables or type of analyzer, and the scope of our invention is not otherwise limited, except as set forth by the following claims.

We claim:

1. A method for obtaining an improved estimate of a property of a material produced in a chemical manufacturing process, in which operation of a chemical reactor is controlled through one or more reactor process variables and in which an on-line analyzer that measures data relating to the material is used, the method comprising the steps of:
    (a) mathematically transforming data obtained from the on-line analyzer to obtain scores correlative to the property of the material; and
    (b) regressing the obtained scores with one or more statistically significant reactor process variables to generate an estimate of the property, provided, that a reactor process variable is not a product physical measurement obtained at or near the on-line analyzer.

2. The method of claim 1 wherein the estimate is used in the control of a polyolefin reactor and the reactor is used to manufacture a polymeric material selected from the group consisting of polymers containing at least fifty weight percent of material originating as propylene monomer units, and polymers containing at least fifty weight percent of material originating as ethylene monomer units.

3. The method of claim 1 wherein a nuclear magnetic resonance spectrometer is used to obtain free induction decay curve data which is mathematically transformed to obtain scores, and in which the scores are regressed with the one or more process variables for the purpose of estimating melt flow rate of the polymeric material.

4. The method of claim 1 wherein the on-line analyzer is selected from the group consisting of nuclear magnetic resonance, near infrared, infrared, ultraviolet-visible, X-ray fluorescence, ultrasonic, and Raman spectrometers.

5. The method of claim 1 wherein at least a portion of the chemical manufacturing process occurs in a chemical reactor.

6. The method of claim 5 wherein the chemical reactor is selected from the group consisting of gas phase fluidized bed reactors, gas phase subfluidized bed reactors, stirred tank reactors, liquid pool reactors, gas loop reactors having one or more fluidization domains, and supercritical loop reactors.

7. The method of claim 6 wherein the on-line analyzer is a nuclear magnetic resonance spectrometer, and the scores are obtained by mathematically transforming free induction decay curves from the spectrometer.

8. The method of claim 5 wherein nuclear magnetic resonance spectrometer is used to obtain data which is mathematically transformed to obtain scores which are regressed with one or more process variables for the purpose of estimating a melt flow rate of a polymeric material.

9. The method of claim 8 wherein the process employs a polyolefin reactor, and the polymeric material is selected from the group consisting of polymers containing at least fifty weight percent of material originating as propylene monomer units and polymers containing at least fifty weight percent of material originating as ethylene monomer units.

10. The method of claim 9 wherein the polymeric material is an impact copolymer comprising polymerized propylene and ethylene monomer units.

11. The method of claim 9 wherein the polymeric material comprises at least fifty weight percent of material originating as propylene monomer units and at least two weight percent of material originating as monomer units of an olefin other than propylene or an alpha olefin having four or more carbon atoms.

12. The method of claim 9 wherein the polymeric material comprises at least fifty weight percent of material originating as ethylene monomer units and at least two weight percent of material originating as monomer units of propylene or an alpha olefin having four or more carbon atoms.

13. The process of claim 1 wherein the regression is a non-linear regression.

14. The process of claim 1 wherein the regression is a linear regression.

15. The process of claim 1 wherein at least one of the at least one process variable is a reactor process variable selected from the group consisting of Al/Mg ratio, first reactor catalyst yield, second reactor incremental catalyst yield, first reactor off gas temperature, hydrogen to propylene ratio for the first reactor, hydrogen to propylene ratio for the second reactor, ethylene to propylene ratio for the second reactor, and percent rubber in a final impact copolymer product.

16. A chemical manufacturing process comprising the steps of:
    (a) using an on-line analyzer to collect data related to a chemical material at a point within the manufacturing process;
    (b) mathematically transforming the data to produce scores related to a property of interest of the chemical material;
    (c) regressing the scores with one or more statistically significant reactor process variables to produce an estimate of the property of interest for the chemical material; and
    (d) inputting the estimated property into a controller used in the chemical manufacturing process, provided, that a reactor process variable is not a product physical measurement obtained at or near the on-line analyzer.

17. The process of claim 16 further comprising the step of varying the output of the controller in response to the inputted estimated property to cause the property of interest to move toward a desired value.

18. The process of claim 17 wherein the controller is selected from the group consisting of PID and fuzzy logic controllers.

19. The process of claim 18 wherein there are at least two or more controllers selected from the group of PID controllers, fuzzy logic controllers, and combinations thereof.

20. The process of claim 16 wherein the process includes a chemical reactor and one or more process variables are reactor process variables.

21. The process of claim 20 wherein the chemical reactor is selected from the group consisting of gas phase fluidized bed reactors, gas phase subfluidized bed reactors, stirred tank reactors, liquid pool reactors, gas loop reactors having one or more fluidization domains, and supercritical loop reactors.

22. The process of claim 21 wherein the data collected comprise free induction decay curves obtained from a nuclear magnetic resonance spectrometer, and wherein the property of interest is melt flow rate.

23. The process of claim 20 wherein the process employs a polyolefin reactor to manufacture a polymeric material, and the polymeric material is selected from the group consisting of polymers containing at least fifty weight percent of material originating as propylene monomer units and polymers containing at least fifty weight percent of material originating as ethylene monomer units.

24. The process of claim 20 wherein the chemical manufactured in the chemical manufacturing process comprises a polymeric chemical selected from the group consisting of terephthalic acid, polystyrene, polyethylene, polypropylene, polymers of alpha-olefin monomers containing from 4 to 20 carbon atoms, polyvinyl chloride, polyethylene terephthalate, and combinations thereof.

25. The process of claim 16 wherein the on-line analyzer is selected from the group consisting of nuclear magnetic resonance, near infrared, infrared, ultraviolet-visible, X-ray fluorescence, ultrasonic, and Raman spectrometers.

26. The process of claim 16 wherein the data collected comprise free induction decay curves obtained from a nuclear magnetic resonance spectrometer.

27. The process of claim 26 wherein the property of interest is melt flow rate.

* * * * *